United States Patent
Fujimoto

(10) Patent No.: US 6,391,327 B1
(45) Date of Patent: May 21, 2002

(54) PESTICIDAL COMPOSITION

(75) Inventor: Izumi Fujimoto, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/637,702

(22) Filed: Aug. 15, 2000

Related U.S. Application Data

(62) Division of application No. 09/287,121, filed on Apr. 7, 1999, now Pat. No. 6,255,340.

(30) Foreign Application Priority Data

Apr. 9, 1998 (JP) .............. 10-097565

(51) Int. Cl.$^7$ .............. A01N 25/00; A01N 43/40; A01N 43/54; A01N 43/50; C07D 401/00; C07D 237/00; C07D 279/00

(52) U.S. Cl. .............. 424/405; 514/277; 514/256; 514/226.8; 514/336; 514/340; 514/385; 514/396; 514/397; 424/409; 546/268.1; 546/268.4; 546/268.7; 544/242; 544/297; 544/53; 544/59; 544/60

(58) Field of Search .............. 514/227.2, 396, 514/397, 336, 226.8, 385; 424/405, 409; 544/297, 242, 53, 59, 60; 546/268.1, 268.4, 268.7

(56) References Cited

U.S. PATENT DOCUMENTS

| | | | |
|---|---|---|---|
| 4,742,060 A | 5/1988 | Shiokawa et al. | 514/252 |
| 4,849,432 A | 7/1989 | Shiokawa et al. | 514/341 |
| 5,034,405 A | 7/1991 | Hideki et al. | 514/365 |
| 5,304,566 A | 4/1994 | Ishimitsu et al. | 514/357 |
| 5,532,365 A | 7/1996 | Kodaka et al. | 544/212 |
| 5,750,548 A | 5/1998 | Friedel et al. | 514/357 |

FOREIGN PATENT DOCUMENTS

EP 0428941 A1 5/1991

OTHER PUBLICATIONS

Arvai et al. (DN 127:81238, abstract of WO 9719040), 1997.*
Nagata et al. (Med. Entomol. Zool. (1997), 48(2), 135–139).*

* cited by examiner

Primary Examiner—Sabiha Qazi
(74) Attorney, Agent, or Firm—Birch, Stewart, Kolasch & Birch, LLP

(57) ABSTRACT

A pesticidal composition comprising prallethrin and a neonicotinoid compound given in the following formula (1), (2) or (3), as an active ingredient

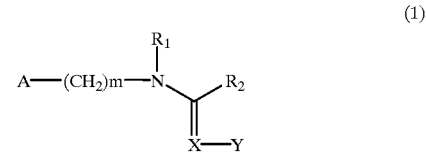

(1)

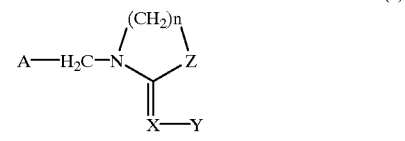

(2)

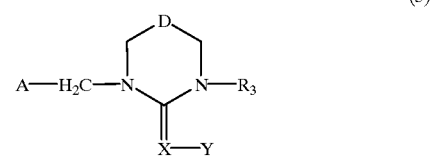

(3)

wherein, A represents a 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group; $R_1$ represents a hydrogen atom, methyl, ethyl, formyl or acetyl group; $R_2$ represents a methyl, amino, methylamino, N,N-dimethylamino, ethylamino, N,N-diethylamino, N-methyl-N-ethylamino, 1-pyrrolidinyl, (6-chloro-3-pyridyl) methylamino or N-methyl-N-(6-chloro-3-pyridyl)methylamino group; $R_3$ represents a methyl, ethyl, propyl, propenyl or propynyl group; X represents a nitrogen atom or CH group; Y represents a cyano, nitro or trifluoroacetyl group; Z represents a NH group or sulfur atom; D represents an oxygen atom or —N(CH$_3$)— group; m represents 0 or 1; and n represents 2 or 3, has an excellently effective for controlling pests.

18 Claims, No Drawings

PESTICIDAL COMPOSITION

This application is a divisional of application Ser. No. 09/287,121, filed on Apr. 7, 1999, now U.S. Pat. No. 6,255,340 the entire contents of which are hereby incorporated by reference.

FIELD OF THE INVENTION

The present invention relates to a pesticidal composition which comprises prallethrin and a neonicotinoid compound as active ingredients.

BACKGROUND OF THE INVENTION

Prallethrin is a known insecticidal compound and described in The Pesticide Manual $10^{th}$ edition, page 827 (British Crop Protection Council 1994). Its chemical name is (S)-2-methyl-4-oxo-3-prop-2-ynylcyclopent-2-enyl (1R)-cis,trans-2,2-dimethyl-3-(2-methylprop-1-enyl) cyclopropanecarboxylate. Neonicotinoid compounds include amidine compounds and guanidine compounds having a nitro, cyano or trifluoroacetyl group, and described in, for example, U.S. Pat. No. 5,532,365, U.S. Pat. No. 4,742,060, U.S. Pat. No. 4,849,432, U.S. Pat. No. 5,034,404, U.S. Pat. No. 5,750,548, 5,304,566, EP-428941A and so on.

SUMMARY OF THE INVENTION

The present invention provides a pesticidal composition that is effective for controlling harmful pests, especially arthropods.

The present composition comprises prallethrin and the neonicotinoid compound described below as active ingredients and clearly shows a synergistic effect. The neonicotinoid compounds utilized in the present invention are represented in the following formulas (1), (2) or (3):

$$A-(CH_2)_m-\underset{\underset{X=Y}{|}}{N}\overset{R_1}{\underset{R_2}{<}} \quad (1)$$

$$A-H_2C-\underset{\underset{X=Y}{|}}{N}\overset{(CH_2)_n}{\underset{Z}{<}} \quad (2)$$

$$A-H_2C-N\overset{D}{\underset{\underset{X=Y}{|}}{\diagup\diagdown}}N-R_3 \quad (3)$$

wherein,

A represents a 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group;

$R_1$ represents a hydrogen atom, methyl, ethyl, formyl or acetyl group;

$R_2$ represents a methyl, amino, methylamino, N,N-dimethylamino, ethylamino, N,N-diethylamino, N-methyl-N-ethylamino, 1-pyrrolidinyl, (6-chloro-3-pyridyl)methylamino or N-methyl-N-(6-chloro-3-pyridyl)methylarmino group;

$R_3$ represents a methyl, ethyl, propyl, propenyl or propynyl group;

X represents a nitrogen atom or CH group;

Y represents a cyano, nitro or trifluoroacetyl group;

Z represents a NH group or sulfur atom;

D represents an oxygen atom or —N(CH₃)— group;

m represents 0 or 1; and n represents 2 or 3.

DETAILED DESCRIPTION OF THE INVENTION

The examples of the neonicotinoid compounds of the formula (1) in the present composition include (E)-$N^1$-[(6-chloro-3-pyridyl)methyl]-$N^2$-cyano-$N^1$-methylacetamidine, N-[(6-chloro-3-pyridyl)methyl]-N-ethyl-N'-methyl-2-nitro-1,1-ethylidenediamine, 1-(6-chloro-3-pyridyl)methyl-3-methyl-2-cyanoguanidine, 1-(6-chloro-3-pyridyl)methyl-1,3-dimethyl-2-cyanoguanidine, 1-(6-chloro-3-pyridyl)methyl-1-ethyl-3-methyl-2-cyanoguanidine, 1-(6-chloro-3-pyridyl)methyl-1,3-dimethyl-3-(6-chloro-3-pyridyl)methyl-2-cyanoguanidine, 1-(6-chloro-3-pyridyl)methyl-3-methyl-2-nitroguanidine, 1-(6-chloro-3-pyridyl)methyl-3,3-dimethyl-2-nitroguanidine, 1-(6-chloro-3-pyridyl)methyl-1-methyl-2-nitroguanidine, 1-(6-chloro-3-pyridyl)methyl-1,3-dimethyl-2-nitroguanidine, 1-(6-chloro-3-pyridyl)methyl-3-ethyl-2-nitroguanidine, 1-(6-chloro-3-pyridyl)methyl-3-(6-chloro-3-pyridyl)methyl-2-nitroguanidine, 1-(6-chloro-3-pyridyl)methyl-3-methyl-2-trifluoroacetylguanidine, 1-(6-chloro-3-pyridyl)methyl-1-ethyl-3-methyl-2-nitroguanidine, 1-(6-chloro-3-pyridyl)methyl-1,3,3-trimethyl-2-nitroguanidine, 1-(6-chloro-3-pyridyl)methyl-2-nitroguanidine, 1-(6-chloro-3-pyridyl)methyl-1-ethyl-2-nitroguanidine, 1-(3-pyridyl)methyl-3-methyl-2-nitroguanidine, 1-(6-bromo-3-pyridyl)methyl-3-methyl-2-nitroguanidine, 1-(2-chloro-5-thiazolyl)methyl-3-methyl-2-nitroguanidine, 1-(3-cyanophenyl)-3-methyl-2-nitroguanidine, 1-(4-chlorophenyl)methyl-3-methyl-2-nitroguanidine, 1-(6-chloro-3-pyridyl)methyl-3,3-dimethyl-1-formyl-2-nitroguanidine, 1-(6-chloro-3-pyridyl)methyl-3,3-dimethyl-1-acetyl-2-nitroguanidine, 1-(6-chloro-3-pyridyl)-3-methyl-2-cyanoguanidine, 1-(2-chloro-5-thiazolyl)methyl-3,3-dimethyl-2-nitroguanidine, 1-(2-chloro-5-thiazolyl)methyl-1-ethyl-3-methyl-2-nitroguanidine, 1-(2-chloro-5-thiazolyl)methyl-1-acetyl-3,3-dimethyl-2-nitroguanidine, 1-(6-chloro-3-pyridyl)methyl-1-methyl-2-trifluoroacetylguanidine, 1-(2-chloro-5-thiazolyl)methyl-1,3-dimethyl-2-nitroguanidine, 1-(2-chloro-5-thiazolyl)methyl-1-methyl-2-nitroguanidine, 1-(5-thiazolyl)methyl-3-methyl-2-nitroguanidine, 1-(2-methyl-5-thiazolyl)methyl-3,3-dimethyl-2-nitroguanidine, 1-(2-methyl-5-thiazolyl)methyl-3-methyl-2-nitroguanidine, 1-(2-phenyl-5-thiazolyl)methyl-3-methyl-2-nitroguanidine, 1-(2-chloro-5-thiazolyl)methyl-3,3-diethyl-2-nitroguanidine, 1-(2-chloro-5-thiazolyl)methyl-3-methyl-3-ethyl-2-nitroguanidine, 1-(2-chloro-5-thiazolyl)methyl-3-(1-pyrrolidinyl)-2-nitroguanidine, 1-(2-chloro-5-thiazolyl)methyl-1,3,3-trimethyl-2-nitroguanidine, 1-(2-bromo-5-thiazolyl)methyl-3-methyl-2-nitroguanidine, 1-(2-bromo-5-thiazolyl)methyl-3,3-dimethyl-2-nitroguanidine, 1-(2-chloro-5-thiazolyl)methyl-3-methyl-2-cyanoguanidine, 1-(tetrahydrofuran-3-yl)methyl-3-methyl-2-nitroguanidine and 1-(tetrahydrofuran-2-yl)methyl-3-methyl-2-nitroguanidine.

The examples of the neonicotinoid compounds of the formula (2) in the present composition include 1-[(6-chloro-3-pyridyl)methyl]-N-nitro-2-imidazolidineimine, 3-[(6-chloro-3-pyridyl)methyl]-N-cyano-2-thiazolidineimine and 1-[(6-chloro-3-pyridyl)methyl]-N-nitrotetrahydropyrimidine-2-imine.

The examples of the neonicotinoid compounds of the formula (3) in the present composition include 3-[(2-chloro-5-thiazolyl)methyl]-5-methyl-4-nitroiminotetrahydro-1,3,5-oxadiazine, 3,5-dimethyl-1-[(6-chloro-3-pyridyl)methyl]-2-nitroiminohexahydro-1,3,5-triazine, 3,5-dimethyl-1-[(2-chloro-5-thiazolyl)methyl]-2-nitroiminohexahydro-1,3,5-triazine, 3-ethyl-5-methyl-1-[(6-chloro-3-pyridyl)methyl]-2-nitroiminohexahydro-1,3,5-triazine, 3-n-propyl-5-methyl-1-[(6-chloro-3-pyridyl)methyl]-2-nitroimino hexahydro-1,3,5-triazine, 3-n-propyl-5-methyl-1-[(2-chloro-5-thiazolyl)methyl]-2-nitroiminohexahydro-1,3,5-triazine, 3-(2-propenyl)-5-methyl-1-[(6-chloro-3-pyridyl)methyl]-2-nitroiminohexahydro-1,3,5-triazine and 3-(2-propynyl)-5-methyl-1-[(6-chloro-3-pyridyl)methyl]-2-nitroiminohexahydro-1,3,5-triazine.

The targeted pests controlled by the present composition are, for example, the following arthropods:
pillbugs and Isopoda (sowbugs) such as *Oniscus asellus, Armadillidium vulgare* (Latreille pillbug) and *Porcellio scarber*; Diplopoda such as *Blanilus guttulatus* (millepede); Chilopoda such as *Geophilus carpophagus*, Scutigera spp., *Scolopendra subspini* and Thereunema spp.; Symphyla such as *Scutigerella immaculata*; Thysanura (bristletails) such as *Ctenolepisma villosa* (oriental silverfish) and *Lepisma saccharina* (silverfish); Psocoptera such as *Trogium pulsatorium* (larger pale booklice); Collembola (snowfleas) such as *Onichiurus armatus*; Isoptera (termites) such as Mastotermitidae, Termopsidae (e.g. Zootermopsis, Archotermopsis, Hodoterrnopsis, Porotemes), Kalotermitidae (e.g. Kalotermes, Neotermes, Cryptotermes, Incisitermes, Glyptoterrmes), Hodoterrnitidae (e.g. Hodotermes, Microhodotermes, Anacanthotermes), Rhinotermitidae (e.g. Reticulitermes, Heteroterrnes, Coptotermes, Schedolinotermes), Serriterrnritidae and Termitidae (e.g. Amitermes, Drepanotermes, Hopitaliterrmes, Trinervitermes, Macrotermes, Odontotermes, Microtermes, Nasutitermes, Pericapritermes, Anoplotermes); Dictyoptera (cockroaches) such as *Blatta orientalis* (oriental cockroach), *Periplaneta americana* (American cockroach), Periplaneta fuliginosa (smokybrown cockroach), *Leucophaea maderae* and *Blattella germanica* (German cockroach); Orthoptera such as Gryllotapa spp. (mole cricket), *Acheta domesticus, Teleogryllus emma* (field cricket), *Locusta migratoria* (asiatic locust/oriental migratory locust), *Melanoplus differentialis* and *Schistocera gregaria*; Dermaptera (earwigs) such as *Labidura riparia* and *Forficula auricularia*; Anoplura such as *Phthirus pubis, Pediculus humanus, Haematopinus sulus*, Linognathus spp. and Solenopotes spp.; Mallophaga such as Trichodectes spp., Tromenopon spp., Bovicola spp. and Felicola spp.; Thysanoptera (thrips) such as *Frankiniella intonsa* (flower thrips), onion thrips, *Thrips tabaci* (cotton seedling thrips) and *Thripspalmi*; Heteroptera such as Nezara spp., Eurygaster spp., *Dysdercus intermedius, Cimex lectularis*, Triatoma spp., *Rhodnius prolixus, Nezara antennata* (green stink bug) and *Cletus puncttiger*; Homoptera such as *Aleurocanthus spiniferus* (citrus spiny whitefly), *Bemisia tabaci* (sweetpotato whitefly), *Trialeurodes vaporariorum* (greenhouse whitefly), cotton asphid, *Aphis gossypii* (melon aphid), *Brtevicoryne brassicae* (cabbage asphid), *Cryptomyzus ribis, Aphis fabae, Macrosiphum euphorbiae* (potato aphid), *Myzus persicae* (green peach aphid), *Phorodon humuli*, Empoasca spp., *Nephootettix cincticeps* (green rice leafhopper), *Lecanium corni* (brown scale), *Saissetia oleae* (black scale), *Laodelphax striatellus* (small brown plant hopper), *Nilaparvata lugens* (brown rice planthopper), *Aonidiella aurantii* (red scale), *Aspidiotus hederae* (ivy scale), Pseudococcus spp., Psylla spp. and *Phylloxera vastrix*; Lepidoptera such as *Pectinophora gossypiella* (pink bollworm), *Lithocolletis blancardella, Plutella xyloste* (diamondback moth), *Malacosoma neustria* (tent catapillar), *Euproctis subflava* (oriental tussock moth), *Lymantria dispar* (gypsy moth), *Bucculatrixpyrivorella* (pear leafniner), *Phyllocnistis citrella* (citrus leatniner), Agrotis spp., *Euxoa spp., Earias insulana*, Heliothis spp., *Spodoptera exigua* (beet armyworm), *Spodoptera litura* (common cutworm), Spodoptera spp., *Mamestra brassicae* (cabbage armyworm), *Trichoplusia ni, Carpocapsa pomonella*, Pieris spp., Chilo spp., *Pyrausta nubilalis, Ephestia kuehniella* (Mediterranean flour moth), *Galleria mellonella* (greater wax moth), *Tineola bisselliella* (webbing clothes moth), *Tenea translucens*, oriental tea tortrix (*Homona magnanima*) and *Totrix viridana*; Coleoptera (beetles) such as *Anobium punctatum, Rhizopertha dominica* (lesser grain borer), *Acanthoscelides obectus* (bean weevil), *Agelastica alni, Leptinotarsa decemlineata, Phaedon cochleariae*, Diabrotica spp., *Psylliodes angusticollis* (solanum flea beetle), *Phyllotreta striolata* (striped flea beetle), Epilachna spp., Atomaria spp., *Oryzaephilus surinamensis* (sawtoothed grain beetle), Anthonomus spp., sitophilus spp., *Otriorhynchus sulcatus* (black vine weevil), *Cosmopolites sordidus* (banana weevil borer), *Ceuthorhyncidius albosuturalis, Hypera postica* (alfalfa weevil), Dermestes spp., Trogoderma spp., *Attagenus unicolor* (black carpet beetle), Lyctus spp., *Meligethes aeneus*, Ptinus spp., *Gibbium psylloides*, Tribolium spp., *Tenebrio molitor* (yellow mealworm), Agriotes spp., *Melolontha mololontha*, Scolytidae (e.g. Xyleborus and Scolytoplatypus), Cerambycidae (e.g. Monochamus, Hylotrupes, Hesperophanus, Chlorophorus, Palaeocallidium, Semanotus, Purpuricenus, Stromatium), Platypodidae (e.g. Crossotarsus, Platypus), Bostrychidae (e.g. Dinoderus, Bostrychus, Sinoderus), Anobiidae (e.g. Ernobius, Anobium, Xyletinus, Xestobium, Ptilinus, Nicobium, Ptilineurus) and Buprestidae; Hymenoptera such as Diprion spp., Hoplocampa spp., Lasius spp., *Formica japonica*, Vespa spp., and Siricidae (e.g. Urocerus, Sirex); Diptera such as Aedes spp., Anopheles spp., Culex spp., *Drosophila melanogaster, Musca domestica* (housefly), Fannia spp., Calliphora spp., Lucilia spp., Chrysomya spp., Cuterebra spp., Gastrophilus spp., Stomoxys spp., Oestrus spp., Hypoderma spp., Tabanus spp., *Bibio hortulanus, Pegomyia hyoscyami, Ceratitus capitata, Dacus dorsalis* (oriental fruit fly), Tipula paludosa, Simulium spp., Eusimulium spp., Phlebotomus spp., Culicoides spp., Chrysops spp., Haematopota spp., Braula spp., Morellia spp., Glossina spp., Wohlfahrtia spp., Sarcophaga spp., Lipoptena spp., Melophagus spp. and Muscina spp.; Siphonaptera such as *Xenopsylla cheopis*, Ceratophyllus spp., Pulex spp. (human flea) and Ctenocephalides spp. (cat flea/dog flea); Arachnida such as *Scorpio maurus, Latrodectus mactans* and Chiracanthium spp.; mites such as Otodectus spp., *Acarus siro* (grain mite), Argas spp., Ornithodoros spp., Ornithonyssus spp., Dermanyssus spp., Eriophyes spp., *Chelacaropsis moorei*, Dermatophagoides spp., *Psoroptes equi*, Chorioptes spp., Saracoptes spp., Tarsonemus spp., clover mite (*Bryobia praetiosa*), Panonychus spp., Tetranychus spp. (spider mites), Raillietas spp., Pneumonyssus spp., Sternostorma spp., Acarapis spp., Cheyletiella spp., Myobia spp., Psorergates spp., Demodex spp., Trombicula spp., Listrophorus spp., Tyrophagus spp., Sarcoptes spp., Notoedres spp., Cytodides spp., Laminosioptes spp.; and the like.

For the present invention, the mixing ratio of prallethrin and the neonicotinoid compounds is the ratio wherein prallethrin and the neonicotinoid compounds show a synergistic effect, and usually from 100:1 to 1:100 parts by weight, preferable within the range from 10:1 to 1:10.

The present composition may be prepared only from prallethrin and the neonictinoid compounds, but for practical uses, the present composition is utilized usually as a formulation that appropriately contains an inert carrier. Therefore, the present composition usually comprises solid carriers, liquid carriers, auxiliaries or the like as well as prallethrin and the neonictinoid compounds. Suitable forms of formulation include liquid formulations such as emulsifiable concentrates, oil formulation and suspensible concentrates, dust, wettable powder, granules, paste formulation, microencapsulated formulation, foaming formulation, aerosol, liquid carbon dioxide solution and sheet formulation. The amount of prallethrin and neonicotinoid compounds incorporated depends on the formulation form, but the total content of prallethrin and neonicotinoid compounds is usually from 0.005 to 50% by weight.

The above-mentioned formulations may be obtained by standard methods, for example, mixing prallethrin and neonicotinoid compounds with solid or liquid carrier(s), and optionally, adding auxiliaries such as emulsifiers or adhesives. As the carrier that is used in the situation of formulating, the following are suitable.

Suitable solid carriers include, for example, natural-occurring or synthetic minerals such as clay, kaolin, talc, bentonite, sericite, quartz, sulfur, active carbon, calcium carbonate, diatomaceous earth, pumice, calcite, sepiolite, dolomite, silica, alumina, vermiculite and perlite, as well as powdered forms of sawdust, an ear of corn, palm tree coconut shells and tobacco stems. Suitable liquid carriers include, for example, aromatic or aliphatic hydrocarbons such as xylene, toluene, alkylnaphthalene, phenylxylylethane, kerosene, gas oil, hexane and cyclohexane; halogenated hydrocarbons such as chlorobenzene, dichloromethane, dichloroethane and trichloroethane; alcohols such as methanol, ethanol, isopropyl alcohol, butanol and hexanol; ethers such as diethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrile and isobutyronitrile; dimethylsulfoxide; amides such as N,N-dimethylformamide and N,N-dimethylacetamide; botanical oils such as soybean oil and cottonseed oil; water; and so on.

Suitable auxiliaries for formulation include, for example, nonionic emulsifiers such as polyoxyethylene fatty acid esters and polyoxyethylene fatty acid alcohol ethers; ionic emulsifiers such as alkylsulfonic acid salts, alkylsulfuric acid salts and arylsulfonic acid salts; dispersing agents such as ligninsulfonic acid salts and methylcellulose; adhesives such as carboxymethyl cellulose, gum arabic, polyvinyl alcohol and polyvinyl acetate; and coloring agents such as iron oxide, titanium oxide, Persian blue, alizarine dye, azo dye and phthalocyanine dye.

Moreover, the present composition may comprise active ingredients other than prallethrin and the neonicotinoid, or synergists such as piperonyl butoxide (PBO), octachlorodipropyl ether (S421), N-(2-ethylhexyl)bicyclo[2.2.1]hept-5-ene-2,3-dicarboximide, isobornyl thiocyanatoacetate (IBTA) and N-(2-ethylhexyl)-1-isopropyl-4-methylbicyclo[2.2.2]oct-5-ene-2,3-dicarboximide.

The present composition may be employed usually on the soil or in places wherein harmful arthropods inhabit, but may cooperate in the production of products that controls pests by administering into a synthetic resin sheet or sheathed electric lines. The employed amount is about from 0.001 to 10 mg/m$^3$ of the active ingredients (the total of prallethrin and the neonicotinoid compounds) when the present composition is utilized in a situation of household use, and for example, in the situation of controlling mosquitoes and flies indoors. Furthermore, when controlling ants or cockroaches, the active ingredients are employed at about from 0.001 to 100 mg/m$^3$.

In the case of controlling timber pests such as termites and powderpost beetles, the present invention may be employed directly onto the said pest, but said composition is usually employed on the inhabiting timber or soil of the pest. The employed amount differs upon the sort of objective harmful arthropods, formulation, employed area or employed method, but generally the amount of the active ingredients (prallethrin and neonicotinoid compounds) is about form 0.1 to 10,000 mg/m$^2$.

In addition, in the case the present composition is utilized for agricultural purposes, an amount from 0.1 to 1,000 g/ha of the active ingredients is employed onto the soil, plants, or directly onto the harmful arthropods. In that situation, the present composition is employed as emulsifiable concentrates, suspensible concentrates or wettable powders by dissolving in water usually at about from 1 to 1000 ppm.

EXAMPLES

Below, the present invention is described in detail with the examples.

Formulation Example 1

One part by weight of Tokuseal GU-N (Tokuyama Corp. product) and 5 parts by weight of (E)-N$^1$-[(6-chloro-3-pyridyl)methyl]acetamidine were mixed and pulverized in an centrifugal pulverizer (the powder). Separately, 1 part by weight of prallethrin was dissolved in 9 parts by weight of Solvesso 150 (Exxon product) and absorbed into 7 parts by weight of Tokuseal GU-N (the oil absorption). After mixing the oil absorption and the powder, 4 parts by weight of Sorpol 5060 (Toho Chemical product), 2 parts by weight of Demol SNB (Kao Corp. product) and 71 parts by weight of Fubasami Clay A300 (Fubasami Clay product) were added, and mixed in a mixer to obtain 100 pasts by weight of wettable powder.

Next, the test examples are given.

Test Example 1

One half (0.5)µL of the following acetone dissolving solution wherein the concentration was adjusted to set forth a dosage given below, was applied to the back thoracic region of a housefly (*Musca domestica*) which is resistant to pyrethroid and the mortality was examined 2 days later. The average of the results after repeating the example thrice are given in table 1 and table 2.

TABLE 1

| examined compound(s) | dosage (µg per insect) | mortality (%) |
|---|---|---|
| Prallethrin | 1.25 | 6.7 |
|  | 2.5 | 10 |
|  | 5 | 30 |

TABLE 1-continued

| examined compound(s) | dosage (μg per insect) | mortality (%) |
|---|---|---|
| Compound A*¹ | 1.25 | 15 |
|  | 5 | 15 |
|  | 10 | 5 |
| Prallethrin + | 5 + 5 | 80 |
| Compound A*¹ | 2.5 + 5 | 70 |
|  | 5 + 10 | 100 |
|  | 1.25 + 5 | 60 |
|  | 2.5 + 10 | 95 |
|  | 5 + 1.25 | 95 |

*¹"Compound A": (E)-N¹-[(6-chloro-3-pyridyl)methyl]-N²-cyano-N¹-methylacetamidine

TABLE 2

| examined compound(s) | dosage (μg per insect) | mortality (%) |
|---|---|---|
| Prallethrin | 1.25 | 6.7 |
|  | 2.5 | 10 |
| Compound B*² | 0.625 | 10 |
|  | 1.25 | 45 |
| Prallethrin + | 0.625 + 0.625 | 65 |
| Compound B*² | 1.25 + 1.25 | 90 |
|  | 0.0.625 + 1.25 | 90 |
|  | 0.3125 + 1.25 | 75 |
|  | 0.625 + 2.5 | 85 |
|  | 0.3125 + 2.5 | 90 |
|  | 1.25 + 0.625 | 80 |
|  | 2.5 + 1.25 | 100 |
|  | 2.5 + 0.625 | 100 |

*²"Compound B": 1-(tetrahydrofuran-3-yl)methyl-3-methyl-2-nitroguanidine

Test Example 2

Three (3) cm of soil was packed into the central inner portion of a glass tube that has an inner diameter of 1.7 cm and is 15 cm long, and on one surface of the soil, 0.7 mL of each aqueous solution that has the examined compound formulated to a determined dilution (examined compound and applied concentration given in table 3). Subsequently, 4% agar was inserted onto both surfaces of the soil, 50 worker Formosan subterranean termites (*Coptotermes formosanus*) and 5 soldier Formosan subterranean termites were deposited into side of the inner part of the tube wherein no compound was applied, and the tunneled soil condition by the termites was examined a week later. The example was repeated thrice. The results are given in table 3.

Within the results of table 3, A represents a condition wherein the termites tunneled through the surface of the soil of the treated side and the non-treated side, B represents a condition wherein the surface of the soil of the treated side was tunneled through and the agar was tunneled halfway, C represents a condition wherein the surface of the soil of the treated side was incompletely tunneled through and the agar had no visible tunneling.

TABLE 3

| examined compound(s) | concentration of application (ppm) | results |
|---|---|---|
| composition C*³ + Prallethrin 5EC*⁵ | 100 + 20 | CCC |
| Compound B*² + Prallethrin 5EC*³ | 20 + 50 | CCC |
| Compound D*⁴ + Prallethrin 5EC*³ | 20 + 50 | CCC |
| Composition C*³ | 125 | AAA |
| Compound B*² | 20 | ACA |

TABLE 3-continued

| examined compound(s) | concentration of application (ppm) | results |
|---|---|---|
| Compound D*⁴ | 20 | AAA |
| Prallethrin 5EC*⁵ | 20 | AAA |
|  | 62.5 | AAA |

*²"Compound B": 1-(tetrahydrofuran-3-yl)methyl-3-methyl-2-nitroguanidine
*³"Composition C": 20% flowable of 1-[(6-chloro-3-pyridyl)methyl]-N-nitro-2-imidazolidineimine (Nihon Bayer Agrochem product : Hachikusan FL)
*⁴"Compound D": 3-[(2-chloro-5-thiazolyl)methyl]-5-methyl-4-nitroiminotetrahydro-1,3,5-oxadiazine
*⁵"Prallethrin 5EC": emulsifiable concentrate of 5% prallethrin, 85% xylene and 10% Sorpol SM 200

What is claimed is:

1. A pesticidal composition comprising prallethrin and a neonicotinoid compound given in the following formula (2):

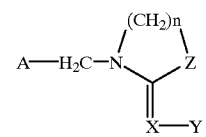

(2)

wherein, A represents a 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group; X represents a nitrogen atom or CH group; Y represents a cyano, nitro or trifluoroacetyl group; Z represents a NH group or sulfur atom; and n represents 2 or 3, as active ingredients, wherein the combination of said prallethrin and said neonicotinoid compound produces a synergistic effect.

2. The pesticidal composition according to claim 1, wherein n represents 2.

3. The pesticidal composition according to claim 2, wherein A represents a 6-chloro-3-pyridyl group.

4. The pesticidal composition according to claim 1, wherein an amount of prallethrin and a neonicotinoid compound is at a weight ratio from 100:1 to 1:100.

5. The pesticidal composition according to claim 4, wherein the neonicotinoid compound is 1-{(6-chloro-3-pyridyl)methyl}-N-nitro-2-imidazolidineimine.

6. A method for controlling pests which comprises applying an effective amount of prallethrin and a neonicotinoid compound given in the following formula (2):

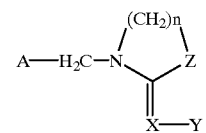

(2)

wherein, A represents a 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group; X represents a nitrogen atom or CH group; Y represents a cyano, nitro or triflouroacetyl group; Z represents a NH group or sulfur atom; and n represents 2 or 3, wherein the combination of said prallethrin and said neonicotinoid compound produces a synergistic effect, to a pest or the locus where a pest inhabits.

7. The method according to claim 6, wherein n represents 2.

8. The method according to claim 7, wherein A represents a 6-chloro-3-pyridyl group.

9. The method according to claim 6, wherein an amount of prallethrin and a neonicotinoid compound is at a weight ratio from 100:1 to 1:100.

10. The method according to claim 9, wherein the neonicotinoid compound is 1-{(6-chloro-3-pyridyl)methyl}-N-nitro-2-imidazolidineimine.

11. The pesticidal composition according to claim 3, wherein n represents 2.

12. The pesticidal composition according to claim 11, wherein X represents a nitrogen atom.

13. The pesticidal composition according to claim 11, wherein the neonicotinoid compound is one selected from 1-[6-chloro-3-pyridyl)methyl]-N-nitro-2-imidazolidineimine, 3-[6-chloro-3-pyridyl)methyl]-N-cyano-2-thiazolidineimine and 1-[6-chloro-3-pyridyl)methyl]-N-nitrotetrahydropyrimidine-2-imine.

14. The method according to claim 8, wherein n represents 2.

15. The method according to claim 14, wherein X represents a nitrogen atom.

16. The method according to claim 6, wherein the neonicotinoid compound is one selected from 1-[6-chloro-3-pyridyl)methyl]-N-nitro-2-imidazolidineimine, 3-[6-chloro-3-pyridyl)methyl]-N-cyano-2-thiazolidineimine and 1-[6-chloro-3-pyridyl)methyl]-N-nitrotetrahydropyrimidine-2-imine.

17. A pesticidal composition comprising prallethrin and a neonicotinoid compound given in the following formula (2):

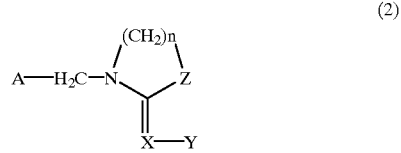

(2)

wherein, A represents a 6-chloro-3-pyridyl group; X represents a nitrogen atom or CH group; Y represents a cyano, nitro or trifluoroacetyl group; Z represents a NH group or sulfur atom; and n represents 2 or 3, as active ingredients, wherein the combination of said prallethrin and said neonicotinoid compound produces a synergistic effect.

18. A method for controlling pests which comprises applying an effective amount of prallethrin and a neonicotinoid compound given in the following formula (2):

wherein, A represents a 6-chloro-3-pyridyl group; X represents a nitrogen atom or CH group; Y represents a cyano, nitro or triflouroacetyl group; Z represents a NH group or sulfur atom; and n represents 2 or 3, wherein the combination of said prallethrin and said neonicotinoid compound produces a synergistic effect, to a pest or the locus where a pest inhabits.

* * * * *